(12) United States Patent
Puglisi et al.

(10) Patent No.: US 9,421,401 B2
(45) Date of Patent: Aug. 23, 2016

(54) DEPOSITION FROM SURFACTANT SYSTEMS

(75) Inventors: Christine Puglisi, Mountainside, NJ (US); Daniel B. Solarek, Hillsborough, NJ (US)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 175 days.

(21) Appl. No.: 13/262,839

(22) PCT Filed: Apr. 12, 2010

(86) PCT No.: PCT/EP2010/054738
§ 371 (c)(1),
(2), (4) Date: Oct. 4, 2011

(87) PCT Pub. No.: WO2010/119000
PCT Pub. Date: Oct. 21, 2010

(65) Prior Publication Data
US 2012/0027831 A1 Feb. 2, 2012

Related U.S. Application Data
(60) Provisional application No. 61/169,483, filed on Apr. 15, 2009.

(30) Foreign Application Priority Data

Jun. 3, 2009 (EP) ..................................... 09161811

(51) Int. Cl.
| | |
|---|---|
| *A61K 8/73* | (2006.01) |
| *A61Q 5/12* | (2006.01) |
| *A61Q 19/10* | (2006.01) |
| *A61Q 13/00* | (2006.01) |
| *A61Q 17/04* | (2006.01) |
| *A61K 8/06* | (2006.01) |
| *A61Q 5/02* | (2006.01) |

(52) U.S. Cl.
CPC . *A61Q 19/10* (2013.01); *A61K 8/06* (2013.01); *A61K 8/732* (2013.01); *A61Q 5/02* (2013.01); *A61Q 5/12* (2013.01); *A61Q 13/00* (2013.01); *A61Q 17/04* (2013.01); *A61K 2800/54* (2013.01); *A61K 2800/5426* (2013.01)

(58) Field of Classification Search
CPC ........... C08B 31/16; A61K 8/732; A61K 8/06
See application file for complete search history.

(56) References Cited

U.S. PATENT DOCUMENTS

| | | | |
|---|---|---|---|
| 4,663,159 A | 5/1987 | Brode, II et al. | |
| 4,977,252 A * | 12/1990 | Chiu .............................. | 536/102 |
| 5,731,430 A | 3/1998 | Fuertes et al. | |
| 6,667,277 B2 | 12/2003 | Hartmann et al. | |
| 2003/0031722 A1* | 2/2003 | Cao et al. ...................... | 424/493 |
| 2005/0003975 A1 | 1/2005 | Browne et al. | |
| 2005/0277768 A1 | 12/2005 | Buwalda et al. | |

FOREIGN PATENT DOCUMENTS

| | | |
|---|---|---|
| CN | 1806038 A | 7/2006 |
| EP | 0 620 0315 A1 | 10/1994 |
| EP | 1743693 A1 * | 1/2007 |
| WO | WO 02/070574 A2 | 9/2002 |
| WO | WO 02/098375 A2 | 12/2002 |
| WO | 2004113485 A1 | 12/2004 |

OTHER PUBLICATIONS

Arif, Economy Premium Shampoos accessed online at http://www.happi.com/contents/view_features/2007-02-06/economy--premium-shampoos/, Aug. 24, 2013.*
QUAB Cationization of Polymers, accessed at http://www.quab.com/docs/QUAB_Brochure.pdf on Aug. 24, 2013.*
"Substantivity", downloaded from http://medical-dictionary.thefreedictionary.com/substantivity downloaded Jan. 26, 2016.*
European Serach Report for Application No. 09161811.6 completion date Nov. 3, 2009.
International Search Report for PCT Application No. PCT/EP2010/054738 dated Jul. 11, 2011.
Modified Starches: Properties and Uses by O.B. Wurzburg, CRC press Boca Raton Florida 1986 (Chapters 8 & 9, pp. 113 and 131 respectively).
English Translation of Chinese Office Action dated Nov. 11, 2012.

* cited by examiner

*Primary Examiner* — Bethany Barham
*Assistant Examiner* — Lisbeth C Robinson
(74) *Attorney, Agent, or Firm* — Norris McLaughlin & Marcus P.A.

(57) ABSTRACT

The invention presented in this application relates to a fragrance deposition system for high surfactant applications such as shampoo and body wash. The system will provide a long lasting release of the fragrance and is more efficient at low levels and does not deposit particles that can cause adverse properties.

16 Claims, No Drawings

DEPOSITION FROM SURFACTANT SYSTEMS

This application is a National Phase Application of PCT Application No. PCT/EP2010/054738, filed Apr. 12, 2010, and claims priority to U.S. Provisional Patent Application Ser. No. 61/169,483, filed on Apr. 15, 2009, and EP Application No. 09161811.6, filed on Jun. 3, 2009, all of which are incorporated herein by reference in their entireties.

FIELD OF INVENTION

The invention as presented herein, involves the deposition of volatile fragrances from an aqueous shampoo or other surfactant system. The challenge is simply put as leaving an oily material on the hair or skin while removing the unwanted dirt and oily residue during the washing process. While if one used excess material some would inevitably be left behind. The ideal situation is to apply very little fragrance from the shampoo (1 percent or less) and still have some fragrance on the hair or skin after leaving the shower or after blow drying.

BACKGROUND OF THE INVENTION

The smell of the shampoo and fragrance of the soaps we use for personal cleansing are a source of relaxation and comfort, whether it be first thing in the morning to help us wake up or for a hot bath to unwind after a hard day. Many new soaps and shampoos are now incorporating aromatherapy essential oils and herbal remedies to assist in relieving stress and providing other health benefits.

No doubt the Personal Care industry is interested in depositing sensorial and/or beneficial ingredients on skin and hair from surfactant containing formulations. Often these ingredients are hydrophobic oils such as fragrances. There is a need for (deposition) systems that in themselves are safe, readily available, renewable, biodegradable, natural or at least lightly modified with chemicals. Modified starches of this invention fill this need. Surprisingly, starch stabilized emulsions prepared according to this invention can stabilize oil-in-water emulsions of the oily ingredients, remain intact in the presence of surfactant solutions and adhere the ingredient to hair or skin.

It would be ideal if those beneficial smells and fragrances were to remain on the skin/hair for a period of time longer so that their aromas could be enjoyed long after one steps out of the shower.

One of skill in the art would realize that if enough of the fragrance oil is added to the shampoo or soap some small percentage of the material will be trapped or absorbed on the surface and provide an extended release of the aroma. This method of achieving long lasting smells is obviously not cost effective as a very high percentage of the fragrance is lost down the drain. In the meantime the surfactants are utilized in the shampoo or soap to remove oily material from the hair (sebum) and skin which are in many respects similar to the fragrances which are ideally left on the substrate.

The manufacturers of these shampoos and soaps would like to use as little of the fragrance oil as possible to be cost effective. Typically these essential oils are formulated at less than one percent in the final shampoo and in some cases significantly less than that. So there is still a huge need in the market place for an effective delivery system for fragrant oils and the like from high surfactant systems such as shampoos and body soaps.

SUMMARY OF THE INVENTION

The use of starch to encapsulate volatile oils and fragrances is well known, such as illustrated in U.S. Pat. No. 6,667,277 to Solarek et al. However the use of these encapsulates has not been used as a means for fragrance delivery from a high surfactant system before. It has now been found that certain modified starches containing both a cationic group and a hydrophobic group on the same backbone can provide the necessary deposition for a shampoo system if the correct modification is accomplished and the molecular weight is in the proper range.

DETAILED DESCRIPTION OF THE INVENTION

The present invention relates to the deposition of volatile fragrance oil from a high surfactant system such as shampoo, facial soap or body wash. The challenge being, leaving a residue of the fragrance oil on the hair or skin while removing the dirt and naturally occurring oils when showering or washing.

It has been found that cationically modified starches can function to assist in the deposition if further modified with a hydrophobic group. In one embodiment of this invention the cationic modification is a trimethyl ammonium derivative of an epoxide or chlorohydrin. Non-limiting examples of such are 3-chloro-2-hydroxypropyltrimethyl ammonium chloride, 2, 3, epoxypropyl trimethylammonium chloride, and the like. The level of treatment on the starch is also important with a minimum of 0.2 weight percent nitrogen bound to the starch backbone, based on the dry weight of starch. Depending on the type of starch used the upper limit will be depended on the processing of the starch and will typically be around 0.6 to 0.9 percent bound nitrogen. In one embodiment of this application the level of nitrogen will be between 0.2 and 0.7 wt % nitrogen based on the dry weight of starch.

The starch modification that accompanies the cationic derivative is prepared by reacting the starch with a long chain alkenyl succinic anhydride reagent. In an embodiment of this application the reagents are octenyl succinic anhydride (OSA) or dodecenyl succinic anhydride (DDSA). In another embodiment of this invention the reagent (OSA or DDSA) is reacted with the starch at from 2, such as between 3 and 10% by weight of the dry starch.

The molecular weight of the starch material is important to the performance of the emulsion and stability in the shampoo. Full molecular weight is too viscous to work with and does not allow for high solids. Low molecular weight does not provide good performance. In an embodiment of this invention, the weight average molecular weight will be between 7 and $90 \times 10^6$. Alternatively stated the starch fluidity range for this embodiment is between a WF=40 and WF=70. Additional information about molecular weight and fluidity can be obtained from "Modified Starches: Properties and Uses" by O. B. Wurzburg, CRC press Boca Raton Fla. 1986.

The starch can be any variety of starch derived from a plant source including and without limitation corn, wheat, rice, potato, tapioca, sorghum, pea, sweet potato and sago. The starch may also be derived by plant breeding or genetic modification to alter the natural ratio of amylose to amylopectin. These starches include, but are not limited to, high amylose (greater than 40% amylose) and low or no amylose starches, such as waxy maize or waxy potato. In one embodiment of this invention the starch will be a native non-high amylose starch containing less than 30% amylose. In another embodiment the starch will be a waxy version of one of the above starches. By waxy version we mean that the starch as isolated from the plant source will have less than 5% amylose.

The base starches may also be physically processed to alter the texture or viscosity of the native starch, such as by thermally processing, physically processing or chemical processing. Thermal processing includes the use of dry heat, drying such as drum drying or spray drying or dextrinization. Physical processing includes the use of roller mills, hammer mills or agglomeration or compact granulation. Chemical modification includes the use of acids and/or bases to gelatinizing or degrading the starch polymers, the action of enzymes to degrade or de-branch the starch, oxidative materials to provide carboxyl groups on the backbone of the starch and functional material such as anionic, non-ionic, hydrophobic and reactive groups. For a comprehensive review of all these modifications see "Modified Starches: Properties and Uses" by O. B. Wurzburg, CRC press Boca Raton Fla. 1986 (Chapters 8 and 9, pages 113 and 131 respectively), which is incorporated herein by reference.

The starches of this invention must be cooked or otherwise made soluble in water. Native starches are not soluble in water without treatment with heat or chemical means. Cooking the starch can be accomplished by applying heat such as in bath cooking, jet cooking (continuous injection of live steam), or as part of a drying process such as drum drying, spray drying and coupled jet cooking with spray drying. In examples where the cooking is accomplished during the drying step, a dry powder is obtained which is considered cold water soluble and requires no further heat. Chemical cooking can also be utilized to render the starch water soluble such as the action of caustic.

To incorporate the active into the starch cook, a significant amount of shear must be applied. Non limiting examples of mixing systems are emulsifiers, turbine mixers, high shear pumps, static mixers, and high pressure injection nozzles. Depending on the type of active, size of the emulsion desired and ratio of starch to active and other considerations, the amount of shear required for each system and application will vary. It has now been found that the use of starches with cationic and hydrophobic derivatives can be used to emulsify fragrance oils such that the oil emulsion is stable in a shampoo formulation for greater than 3 weeks at 43° C. This represents a self life of greater than 6 months at normal room temperature.

Additionally, using starch emulsions to provide the fragrance to the shampoo affords a long lasting release of the fragrance. Most surprisingly is that very low levels of fragrance with the starch, typically less than about 3%, provide much better deposition to the hair or skin than at higher levels. Alternatively stated, the less fragrance you use with the starch system of this invention, the better it works and the longer it lasts. In an embodiment of this invention the fragrance is added as an emulsion in starch and at a rate of less than one percent fragrance per weight of shampoo.

The fragrance can be emulsified into the starch between 20 and 70 percent by weight of the fragrance to dry basis of the modified starch. This value is typically referred to as loading and is usually desirable to have value as high as possible. In one embodiment of this invention the fragrance is encapsulated at 30 to 50 percent based on the dry weight of the starch.

In an embodiment of the invention, the average particle size of the liquid starch emulsion may be about 0.05 microns to about 15 microns, preferably about 0.1 microns to about 10 microns, and more preferably 0.5 to 2.5 microns.

The fragrance of this invention can be derived from synthetic or all natural sources. These include essential oils and blends of synthetic and essential oils. Also included in these fragrances are extracts such as would be found in common plants and herbs such as mint, clove, lavender and tea tree oil. There are literally thousands of oils the fragrance formulator can start with to make a desired smell. All of which are included in this invention as well as complex blends. Even food extracts fall under this definition of fragrance, and in some instances are desirable in hair care produces. Non-limiting examples of these would be vanilla, chocolate, strawberry, and mint.

In addition to the starch and fragrance in the shampoo, many other ingredients are normally present and provide a wide variety of function. These can be, but are not limited to colors, conditioners, active to treat scalp conditions (e.g. dandruff), foam stabilizers, viscosifiers, preservatives, vitamins, herbal extracts, and hair colorants. While these other ingredients serve various functions, they will not interfere with the deposition and long lasting release of the fragrance.

Other applications for this invention would deposit an active from a surfactant system. Some non-limiting examples of surfactant systems are shampoos, body wash, hand soap, bath soap (bar and liquid). Some examples of actives other than fragrances are silicone oil (for moisturizing and conditioning), medications, sunscreen, dyes, and moisturizers. In one embodiment of this invention the active is chosen from the group of fragrances, silicone oil and sunscreen.

The invention will now be illustrated by the following non-limiting examples.

EXAMPLE 1

Three quaternary ammonium cationic starches (waxy base, 0.2% N), one with a WF=40 (sample#2) and the second with a WF=70 (sample #3) and a third with a WF=85 (sample #4), were modified with 10% treatment of OSA. The starches were jet cooked and emulsified with fragrance#1 (a fragrance oil called HW 4950P from Quest International (now Givaudan S.A.) at 30% load (fragrance to starch ratio). The two emulsions were formulated into a shampoo formulation at 2.5% fragrance load. A third sample (control) was generated consisting of fragrance #1 (neat) blended into a shampoo formulation at 2.5% fragrance load. The shampoo formulation was according to the formulation "Clear Conditioning Shampoo 11871-27-1" available from Akzo Nobel Surface Chemistry, Bridgewater, N.J., US and contains:

| Trade Name | INCI Name | % w/w | Supplier |
|---|---|---|---|
| CELQUAT SC-230M polymer | Polyquaternium-10 | 0.25% | AkzoNobel Surface Chemistry |
| Deionized Water | Water (Aqua) | 21.24% | |
| Standapol WAQ-LC | Sodium Lauryl Sulfate | 33.33% | Cognis Corp. |
| Standapol ES-3 | Sodium Laureth Sulfate | 30.00% | Cognis Corp. |
| Tego Betain L7 | Cocamidopropyl Betaine | 10.00% | Goldschmidt |
| Promidium CO | Polypropoxyeth-oxycocamide | 3.18% | Uniqema/Croda |
| Germaben II | Diazolidinyl Urea, Propylene Glycol, Methylparaben, Propylparaben | 1.00% | Sutton Laboratories |
| Sodium Chloride | Sodium Chloride | 1.00% | J. T. Baker |
| Citric Acid | Citric Acid | q.s. | |
| Total: | | 100.00% | | pH: 5.0 to 6.0
Viscosity: 5500-7500 cps (Brookfield, Spindle #4, 20 rpm)

A protocol for washing, rinsing, and drying the hair was developed. Three hair swaths (virgin, brown, European), ordered from "International Hair Importers", were washed with each of the shampoo/fragrance samples. The hair was allowed to dry and after six hours a panel evaluated the fragrance intensity detected from the hair. The rating scale is from 0 (no fragrance) to 5 (very strong). A strong rating would be 2.5 or higher. Table #1 shows that both the low MW starch (WF=70) and the high mw starch (WF=40) yielded fragrance deposition on to the hair that lasted more than 6 hours. The control sample (neat fragrance in shampoo) showed no fragrance depositing/remaining on the hair after 6 hours. The shampoo samples were then put through shelf life stability testing at room temperature (RT) and in an oven set at 43° C. Samples of these shampoo formulations were pulled over a 16 week period, hair was washed and a sensory evaluation performed. As seen in Table #1 and Table #2, the higher mw samples (WF=40) showed no loss in sensory performance over the 16 week period both at RT and 43° C. The lower mw material (WF=70) showed reduced sensory values after 6 (@43° C.) to 10 (RT) weeks. This indicates that the higher molecular weight starches have better stability and protection of the fragrance droplet in the shampoo formulation.

TABLE #1

| Stability Study @ RT - Sensory evaluations after 6 hours | | | |
|---|---|---|---|
| Sample | Fresh (wk = 0) | 6 wk | 16 wk |
| Sample #1 Waxy | Not stable* | N/A | N/A |
| Sample #2 (WF = 40) | 2.5 | 2.7 | 2.6 |
| Sample #3 (WF = 70) | 2.5 | 2.4 | 2.0 |
| Sample #4 (WF = 85) | 1.0 | <0.5 | <0.5 |
| control (@ 2.5%) No starch | <0.5 | <0.5 | <0.5 |

*Emulsion not stable as the starch gelled during preparation

The above table demonstrates that a particular molecular weight (Mw) is most effective for the emulsion stability and deposition of the fragrance.

TABLE #2

| Stability Study @43 C. - Sensory evaluations after 6 hours | | | |
|---|---|---|---|
| Sample | Fresh (wk = 0) | 6 wk | 16 wk |
| Sample #2 (WF = 40) | 2.5 | 2.5 | 2.5 |
| Sample #3 (WF = 70) | 2.5 | 2.0 | 1.9 |
| control (@ 2.5%) | <0.5 | <0.5 | <0.5 |

The above results show that at the higher temperatures, the emulsion continue to be stable and provide good deposition of the fragrance. The elevated temperature (table 2 @ 43° C. for 16 weeks) simulated 1 year stability testing of the full formulation shampoo.

EXAMPLE 2

A starch sample (#5) with a WF=63 lower OSA treatment (5%) and higher cationic treatment (0.66%). The starches were jet cooked and emulsified with fragrance #1 at 30% load (fragrance to starch ration). The emulsions were formulated into a shampoo at 1% fragrance load. A second sample (control) was generate consisting of fragrance #1 (neat) blended into a shampoo at 1% fragrance load. Two hair swaths (virgin, brown, European), ordered from "International Hair Importers", were washed with sample #3 and the control. The hair was allowed to dry and after six hours a panel evaluated the fragrance intensity detected from the hair. The rating scale is from 0 (no fragrance) to 5 (very strong). A strong rating would be 2.5 or higher. The data is shown in Table 3. The shampoo sample was then put through shelf life stability testing at room temperature (RT) and in an oven set at 43° C. Samples of these shampoo formulations were pulled over a 12 week period, hair was washed and a sensory evaluation performed. The stability data at 43° C. is shown in Table 3. Also listed in table #3 is the data for sample #1 added into the shampoo at 1% fragrance.

TABLE #3

| Stability Study at 43° C. - Sensory evaluation after 6 hours | | | |
|---|---|---|---|
| Sample | Fresh (wk = 0) | 10 wk | 12 wk |
| Sample #2 (WF = 40) | 2.0 | 1.3 | 1.0 |
| Sample #5 (WF = 63) | 2.3 | 1.9 | 1.9 |
| Control (@1%) | <0.5 | <0.5 | <0.5 |

The above examples show that by adjusting the ratio of cationic group to hydrophobic group that an equal or better deposition can be obtained while using less of the fragrance in the shampoo. Comparing Table 1 and 2 above wherein the fragrance was present at 2.5% and table 3 where the fragrance was added at 1%.

As shown in Table 3 increasing the cationic/anionic ration on the starch backbone increases deposition of the fragrance droplets onto the hair both at time zero (fresh). It also improves stability of the particles indicated by the higher sensory ratings given sample #3 at 12 weeks.

EXAMPLE 3

Sensory Comparison of Samples for Long Lasting Release

TABLE 4

| Samples with high and low fragrance loading | | | |
|---|---|---|---|
| Sample # | Time (t = 0) | Time (t = 3 hours) | Time (t = 6 hours) |
| Sample 2 @2.5% fragrance | 2.5 | 2.3 | 2.0 |
| Sample 5 @1.0% fragrance | 2.5 | 2.5 | 2.3 |
| Control (2.5% fragrance) | 2.5 | <0.5 | <0.5 |
| Control (1.0% Fragrance) | 2.5 | <0.5 | <0.5 |

This example shows that sample 2 and sample 5 both continue to release the fragrance well past three hours where the control can virtually not be detected. Note the sample 5 with only 1 percent of the fragrance added to the shampoo provided a higher level of sensory activity at the 3 and 6 hours marks than the higher loading (2.5%) of sample 1.

EXAMPLE 4

Treatment of Hair With Neat Fragrance Oil

A small amount of fragrance oil is applied directly to a paper towel to moisten the towel. A swatch of clean and untreated hair is then wiped with the towel containing the neat fragrance oil in order to deposit a small amount of oil onto the hair. The swatch was then suspended in the open air for 6 hours and then evaluated for fragrance intensity. No evidence of fragrance was detected on the hair swatch after the six hours.

TABLE 5 effect of high fragrance oil on sensory evaluation.

| Sample # | Time (t = 0) | Time (t = 3 hours) | Time (t = 6 hours) |
|---|---|---|---|
| Sample 2 @2.5% fragrance | 2.5 | 2.3 | 2.0 |
| Sample 5 @1.0% fragrance | 2.5 | 2.5 | 2.3 |
| Control (2.5% fragrance) | 2.5 | <0.5 | <0.5 |
| Sample 6, no starch (10.0% fragrance) | 2.5 | 1.0 | <0.5 |

This example shows that at high loadings of fragrance in the shampoo it is possible to get some slight extension of the release of fragrance, but no where near the same level of sensory recognition that can be obtained by use of the starches of this invention. At the same time the starches of this invention allow for a much less fragrance to be used and increased sensory recognition. This is of particular interest to environmental concerns, considering that a vast majority of the shampoo gets rinsed down the drain. Given the formulations of this invention, much less fragrance is needed and thus much less is washed down into the environment.

EXAMPLE 5

High Level of Neat Oil Shampoo

A shampoo, sample 6, was formulated as described in example 1 to contain 10 percent of the fragrance oil with no starch added. A second sample (sample 5 from above) was generated with 2.0% starch encapsulated fragrance. Two hair swatches were then washed with each sample and evaluated as in example 2 and the results shown in Table 6 below.

TABLE 6 effect of high fragrance oil on sensory evaluation.

| Sample # | Time (t = 6 hours) |
|---|---|
| Control (2.0% fragrance) | <0.5 |
| Sample 5 @2.0% fragrance | 2.4 |
| Sample 6 @10.0% fragrance | 2.4 |

This example shows that at high loadings of fragrance in the shampoo it is possible to get some release of fragrance. At the same time the starches of this invention allow for much less fragrance to be used and increased sensory recognition. This is of particular interest to environmental concerns, considering that a vast majority of the shampoo gets rinsed down the drain. Given the formulations of this invention, much less fragrance is needed and thus much less is washed down into the environment.

EXAMPLE 6

Sunscreen Deposition from Facial/Body Wash

A starch sample at 40 WF was modified with 10% OSA and 0.2% N. It was slurried in water at 12% solids, jet cooked and then cooled to 50° C. Two sunscreen actives Octycrylene and Avobenzene were blended together in a 1:1 ratio. The mixture was heated to 50° C. and then emulsified into the starch cook at 70% solids (sample 7). The emulsion was cooled to room temperature and then formulated into a facial wash formulation at 11% solids. Porcine skin samples (purchased from Lampire Biological Laboratories) were washed with a mild cleanser, rinsed and patted dry. The skin was placed in a standard fixture and 0.2 g of the facial wash was deposited onto the skin. The product was lathered for 15 seconds and then rinsed for 20 seconds under running warm water, Excess water was patted dry. The skin was removed from the fixture and allowed to dry for one hour at room temperature and then placed back in the fixture. Adhesive tape is placed on the skin; gentle pressure is applied and then peeled off. The adhesive and actives were dissolved off the tape and analyzed by HPLC. The data is shown in table 5. The sample was compared to an existing commercial face wash/deposition product Freeze 24/7 which claims SPF15 deposition. As shown the encapsulated sunscreen had enhanced deposition of the active from facial wash as compared to the control and comparative example.

TABLE 7

Deposition of sunscreen onto skin from body wash.

| Sample | Octocrylene | Avobenzene | OMC (octyl methoxycinnate) |
|---|---|---|---|
| face wash w/out sunscreen (control) | not detected | not detected | — |
| sample 7 | 16 ppm | 16 ppm | — |
| Freeze 24/7 | 0.6 ppm | 0.2 ppm | 0.4 ppm |

EXAMPLE 7

Silicone Deposition from Shampoo

A starch sample with a WF=63 was modified with 0.5% OSA and 0.66% N. The modified starch was slurried at 35% solids, jet cooked and cooled. Silicone (Dow Corning 200 fluid (1000 cst) was emulsified into the starch cook at 50% solids (sample 8 in table 6 below was prepared using the method of sample 5 above). The silicone starch emulsion was mixed into a shampoo formulation at 2% load. A control sample was generated with 2% silicone blended neat into the shampoo. Brown virgin hair swaths (2 g) were washed with one gram of each shampoo sample as per the protocol stated in example 2. The hair samples were submitted for EDS (Electron Dispersive Spectroscopy) analysis of silicone. The results (Table 8) showed the encapsulated sample showed an increase in silicone deposition compared to the control sample.

TABLE 8

Silicon deposition on hair.

| Sample | Silicone |
|---|---|
| control | 0.3% |
| encapsulated silicone Sample 8 | 0.6% |

EXAMPLE 8

Water Fluidity Measurement and Correlation Between WF and Mw

Starch water fluidity ('WF') is measured using a Thomas Rotational Shear-Type Viscometer (manufactured by Arthur H. Thomas Co., Philadelphia, Pa. 19106), standardized at 30 deg. C. with a standard oil having a viscosity of 24.73 mPas, requiring 23.12+/−0.05 seconds for 100 revolutions. Accurate and reproducible measurements of WF are obtained by determining the time which elapses for 100 revolutions at different solids levels depending on the starch's degree of conversion (as the degree of conversion increases, WF increases and viscosity decreases). The procedure used involves slurrying the required amount of starch (e.g., 6.16 g, dry basis) in 100 ml of distilled water in a covered copper cup and heating the slurry in a boiling water bath for 30 minutes with occasional stirring. The starch dispersion is then brought to the final weight (e.g., 107 g) with distilled water. The time required for 100 revolutions of the resultant dispersion at 81-83° C. is recorded and converted to a water fluidity number using the following conversion table:

| Time Required for 100 Revolutions (seconds) | | | | |
|---|---|---|---|---|
| Amount of Starch used (anhydrous, g) | | | | |
| 6.16[a] | 8.80[b] | 11.44[c] | 13.20[d] | Water Fluidity |
| 60.0 | | | | 5 |
| 39.6 | | | | 10 |
| 29.3 | | | | 15 |
| 22.6 | | | | 20 |
| 20.2 | | | | 25 |
| | 33.4 | | | 30 |
| | 27.4 | | | 35 |
| | 22.5 | | | 40 |
| | | 32.5 | | 45 |
| | | 26.8 | | 50 |
| | | 22.0 | | 55 |
| | | | 24.2 | 60 |
| | | | 19.2 | 65 |
| | | | 15.9 | 70 |
| | | | 13.5 | 75 |
| | | | 11.5 | 80 |
| | | | 10.0 | 85 |
| | | | 9.0 | 90 |

For [a], [b], [c] and [d], final weight of each starch solution is 107, 110, 113 and 115 g, respectively.

Prior work has determined the correlation between the molecular weight of fluidity starches (measured by light scattering methods) and their WF.

TABLE 9

Molecular weight vs. WF for degraded corn starch

| Sample # | wf | Mw × 10[6] |
|---|---|---|
| 1 | 39 | 93.5 |
| 2 | 45.2 | 75.5 |
| 3 | 66.1 | 15.4 |
| 4 | 73.0 | 6.42 |

EXAMPLE 9

Evaluation of Amylose Containing Starch

A starch sample (#9) was made from tapioca starch (~18% amylose). The tapioca starch sample with a WF=63 was modified with 5% OSA and 0.66% cationic treatment. The starch was jet cooked and emulsified with fragrance (a fragrance oil called Crafters Choice™ Pure Seduction Type Fragrance Oil 414 available from Wholesale Supplies Plus, Inc. of Broadview Heights, Ohio, and at http://www.fragranceandflavors.com) at 50% load (fragrance to starch ratio). The emulsion was formulated into a shampoo at 1.0% fragrance load (sample #9). A second sample was generated consisting of the Pure Seduction Type Fragrance Oil blended (neat) into shampoo at 1.0% fragrance load (sample #10). Two hair swaths (virgin, brown, European), ordered from "International Hair Importers", were washed, one with shampoo containing sample #9 and one with the shampoo containing sample #10. The hair was allowed to dry and after six hours a panel evaluated the fragrance intensity detected on the hair. The rating scale is from 0 (no fragrance) to 5 (very strong). A strong rating would be 2.5 or higher, a moderate rating would be 2.0 or higher. The data, shown in Table 10 indicates that the amylose containing starch protects and deposits the fragrance onto the hair. It performs comparable to the waxy modified starches in experiments 1, 2, and 3.

TABLE 10

Amylose containing starch Sensory Rating

| Sample # | Sensory Rating |
|---|---|
| #9 (tapioca starch) | 2.6 |
| #10 (control) | <0.5 |

EXAMPLE 10

Measurement of Particle Size of Emulsion

Two samples were prepared in different batches, Sample A and Sample B, of the same starch base structure to measure the particle size of the liquid starch emulsion. Each sample was a waxy corn starch having a WF=63 modified with 5% OSA and 0.66% nitrogen. The starch was jet cooked and emulsified with fragrance #1 at 50% load (fragrance to starch ratio).

The particle size of the liquid starch emulsion was determined by measuring using a BeckmanCoulter LS13 320 Laser Diffraction Particle Size Analyzer with a Universal Liquid Module attachment. The particle size measured was the average of three runs for 60 seconds each with a pump speed of 60%. For each run, the particle size used to calculate the average was the median particle size depicted as the peak of the Gaussian distribution curve generated by the Analyzer. The average particle sizes are listed in Table 11.

TABLE 11

Particle Size of Emulsion

| Sample | Particle size at Time 0 (avg) | Particle size after 3 weeks at RT (avg) |
|---|---|---|
| Sample A (WF = 63) | 0.6 microns | 1.6 microns |
| Sample B (WF = 63) | 0.6 microns | 1.6 microns |
| Sample C (WF = 40) | 1.5 microns | 1.8 microns |
| Sample D (WF = 50) | 1.0 microns | 1.4 microns |

The examples presented above are offered to illustrate the spirit of this invention and are not intended to limit the scope in any way.

We claim:

1. A surfactant system comprising at least one surfactant and an emulsion of a modified starch and a hydrophobic active ingredient, wherein the emulsion is stable without the at least one surfactant, wherein said modified starch is modified with at least one quaternary ammonium cationic derivative and at least one hydrophobic derivative selected from the group consisting of octenyl succinic anhydride and dodecenyl succinic anhydride on the same polymer backbone, wherein the modified starch contains between 0.2 and 0.7 wt. % of cationic nitrogen and between 3 and 10 wt. % of said hydrophobic derivative, based on the dry weight of said modified starch, and wherein the hydrophobic active ingredient is an oil.

2. The composition of claim 1, wherein said hydrophobic active ingredient is present at less than 3% by weight based on the total weight of said system.

3. The composition of claim 1, wherein the hydrophobic active ingredient is emulsified into said modified starch.

4. The composition of claim 3, wherein the emulsion before blending has an average particle size of about 0.05 microns to about 15 microns.

5. The composition of claim 1, wherein the hydrophobic active ingredient is a fragrance oil.

6. The composition according to claim 1, wherein said modified starch has a water fluidity (WF) value of from about 40 to about 70.

7. The composition of according to claim 1, wherein said modified starch is derived from a base starch, and wherein the base starch is selected from the group consisting of starch from corn, tapioca, potato, wheat, rice, pea and mixtures thereof.

8. The composition according to claim 7, wherein the base starch is a waxy starch.

9. The composition according to claim 1, wherein the composition is a shampoo, soap or body wash.

10. The composition according to claim 1, wherein the weight average molecular weight of said modified starch is from about 7 to about $90 \times 10^6$ Daltons.

11. The composition of claim 1, wherein said cationic derivative is derived from reaction of said starch with a trimethyl ammonium derivative of an epoxide or chlorohydrin.

12. The composition of claim 11, wherein the trimethyl ammonium derivative is selected from 3-chloro-2-hydroxypropyltrimethyl ammonium chloride and 2,3 epoxypropyltrimethyl ammonium chloride.

13. The composition of claim 1, wherein the hydrophobic active ingredient is emulsified into the starch at 20-70% by weight relative to the dry basis of the modified starch.

14. The composition of claim 13, wherein said hydrophobic active ingredient is a fragrance oil.

15. The composition of claim 1 wherein the hydrophobic active ingredient is encapsulated at 30-50% by weight relative to the dry basis of the modified starch.

16. The composition of claim 15, wherein said hydrophobic active ingredient is a fragrance oil.

* * * * *